US009783792B2

(12) United States Patent
Zaydenberg et al.

(10) Patent No.: US 9,783,792 B2
(45) Date of Patent: Oct. 10, 2017

(54) PURIFICATION OF BUTYRYLCHOLINESTERASE USING MEMBRANE ADSORPTION

(75) Inventors: Alexander Zaydenberg, Woodland Hills, CA (US); Susan Weber, Los Angeles, CA (US); Patrick Gavit, Covina, CA (US); Laura Lei, Los Angeles, CA (US); Wolfgang Teschner, Vienna (AT); Harald A. Butterweck, Vienna (AT); Ursula Mais-Paul, Vienna (AT); Hans-Peter Schwarz, Vienna (AT)

(73) Assignees: Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 795 days.

(21) Appl. No.: 12/617,578

(22) Filed: Nov. 12, 2009

(65) Prior Publication Data

US 2010/0226907 A1    Sep. 9, 2010

Related U.S. Application Data

(60) Provisional application No. 61/113,899, filed on Nov. 12, 2008.

(51) Int. Cl.
*A61K 38/46* (2006.01)
*C12N 9/18* (2006.01)

(52) U.S. Cl.
CPC ..................... *C12N 9/18* (2013.01)

(58) Field of Classification Search
CPC ..................... C12N 1/00; C12N 9/18
See application file for complete search history.

(56) References Cited

U.S. PATENT DOCUMENTS

| | | | |
|---|---|---|---|
| 4,216,205 A * | 8/1980 | Radowitz .................. | 424/177.1 |
| 2003/0148488 A1* | 8/2003 | Ralston et al. ............. | 435/196 |
| 2006/0063248 A1* | 3/2006 | Lockridge et al. ......... | 435/197 |
| 2006/0194301 A1* | 8/2006 | Doctor et al. .............. | 435/196 |
| 2007/0184045 A1* | 8/2007 | Doctor et al. .............. | 424/94.6 |
| 2008/0207487 A1* | 8/2008 | DeFrees et al. ............ | 514/2 |

FOREIGN PATENT DOCUMENTS

WO    WO 2007/011390 A2    1/2007

OTHER PUBLICATIONS

Depalma, A., "Reducing Downstream Purification Costs, Controlling the Economics of These Activities Is Not as Hard as It Sounds," *Genetic Engineering Biotechnology News*, Jul. 1, 2008, vol. 28, No. 13, 3 pages.
International Search Report mailed on Mar. 1, 2010, for International Application No. PCT/US2009/064264 filed on Nov. 12, 2009, 5 pages.
Lockridge, O. et al., "Comparison of Atypical and Usual Human Serum Cholinesterase, Purification, Number of Active Sites, Substrate Affinity, and Turnover Number," *The Journal of Biological Chemistry*, Jan. 25, 1978, vol. 253, No. 2, pp. 361-366.
Lockridge, O. et al., "Large Scale Purification of Butyrylcholinesterase From Human Plasma Suitable for Injection Into Monkeys; A Potential New Therapeutic for Protection Against Cocaine and Nerve Agent Toxicity," *J. Med. Chem. Biol. Radiol. Def.*, Jul. 2005, vol. 1, No. 3, pp. 1-22.
Saxena, A. et al., "Developing procedures for the large-scale purification of human serum butyrylcholinesterase," *Protein Expression and Purification*, 2008, vol. 61, pp. 191-196.
Von Bonsdorff, L. et al., "Development of a Pharmaceutical Apotransferrin Product for Iron Binding Therapy," *Biologicals*, 2001, vol. 29, pp. 27-37.
Xu, T., "Review, Ion exchange membranes: State of their development and perspective," *Journal of Membrane Science*, 2005, vol. 263, pp. 1-29.
Briefs, K.-G. et al., "Fast Protein Chromatography on Analytical and Preparative Scale Using Modified Microporous Membranes," *Chemical Engineering Science*, 1992, vol. 47, No. 1, pp. 141-149.
Ghosh, R. et al., "Protein separation using membrane chromatography: opportunities and challenges," *Journal of Chromatography A*, 2002, vol. 952, pp. 13-27.
Reif, O-W. et al., "Characterization and application of strong ion-exchange membrane adsorbers as stationary phases in high-performance liquid chromatography of proteins," *Journal of Chromatography A*, 1993, vol. 654, pp. 29-41.
Yang, H. et al., "Purification of a Large Protein Using Ion-Exchange Membranes," *Ind. Eng. Chem. Res.*, 2002, vol. 41, pp. 1597-1602.
Zeng, X., "Membrane Chromatography: Preparation and Applications to Protein Separation," *Biotechnol. Prog.*, 1999, vol. 15, pp. 1003-1019.

\* cited by examiner

*Primary Examiner* — Lisa J Hobbs
(74) *Attorney, Agent, or Firm* — Morgan, Lewis & Bockius LLP

(57) ABSTRACT

The present invention relates to purification of butyrylcholinesterase using anion exchange material, where the butyrylcholinesterase content is enriched at least 10 fold per total protein in the composition.

13 Claims, 7 Drawing Sheets

PURIFICATION OF BUTYRYLCHOLINESTERASE USING MEMBRANE ADSORPTION

CROSS-REFERENCES TO RELATED APPLICATIONS

This application claims priority to U.S. Provisional Application Ser. No. 61/113,899, filed on Nov. 12, 2008, which is incorporated herein by reference.

BACKGROUND OF THE INVENTION

Toxic organophosphorous (OP) agents pose a risk in both civilian and military contexts. OP agents include nerve gases (e.g., soman, sarin, tabun, VX), pesticides, and cocaine. These agents are believed to act by irreversibly inhibiting acetylcholinesterase, which can result in broncho-constriction, respiratory failure, and death. The cholinesterase polypeptides acetylcholinesterase (AChE) and butyrylcholinesterase (BuChE) have been successfully applied following exposure to these agents, as well as prophylactically (Doctor et al. (2001) *Chemical Warfare Agents: Toxicity at low levels*, pp 191-214). In particular, human BuChE has been shown to protect against a wide range of agents. Human BuChE can be used prophylactically without additional post-exposure treatment, and it has a long half-life in humans, rodents, and primates (Ostergaard et al. (1988) *Acta Anaesth. Scand.*, 32:266-69; Raveh et al. (1993) *Biochem. Pharmacol.* 45:2465-74; Raveh et al. (1997) *Toxicol. Appl. Pharmacol.* 145:43-53; Allon et al. (1998) *Toxicol. Sci.* 43:121-28). Because the enzyme comes from a human source, the risk of an adverse immune response is minimized.

Previous efforts at purifying cholinesterase enzymes have relied on anion column chromatography from plasma or Cohn Fraction IV paste (see e.g., Grunwald et al. (1997) *J. Biochem. Biophys. Methods* 34:123-35; Lockridge et al. (2005) *J Med Chem Biol Radiol.* 3:nihms5095). For large-scale production these methods would require employing cumbersome chromatography column packing procedures and large amounts of buffers.

BRIEF SUMMARY OF THE INVENTION

The present invention is based on the finding that large amounts of cholinesterase proteins can be purified with high efficiency using anion exchange membranes. Membranes offer a number of advantages over column chromatography for large-scale protein purification. Membranes can tolerate faster flow rates, reducing the process time for purification. Membranes have higher dynamic binding capacity, so that smaller adsoption media volumes are used for the same amount of total protein loaded. In addition, smaller volumes of buffers will be required per lot produced. Membranes are easier to scale up than columns, making pilot scale developments and optimization efforts more predictable and relevant for large scale manufacturing processes. Membranes are also easier to use as they do not require cumbersome packing procedures associated with large production scale columns.

In some embodiments, the invention provides methods of making an enriched butyrylcholinesterase (BChE) composition from a biological source having BChE, comprising the steps of applying the biological source having BChE to an anion exchange material; washing the material; and eluting BChE from the anion exchange material, wherein the BChE is enriched after anion exchange at least 10 fold per total protein in the composition as measured by activity per total protein. In some embodiments, BChE is enriched at least 20, 40, 60, 70, 80, 90, 100, 150, 200, or more per total protein, as measured by activity per total protein. In some embodiments, the method is applied to large-scale production of BChE.

In some embodiments, the biological source is a biological fluid, for example, blood or a blood fraction. In some embodiments, the biological fluid is selected from the group consisting of plasma, serum, and Cohn fraction IV or subfractions thereof. In some embodiments, the biological source is milk (e.g., from a transgenic animal), a transgenic plant or plant cell, or a recombinant cell. In some embodiments, the recombinant cell is a HEK, COS, C127, or CHO cell. In some embodiments, the biological source is an organ, e.g., liver or kidney. In some embodiments, the biological source is a mammal, e.g., human, rabbit, horse, monkey, cow, goat, sheep, rat, or mouse.

In some embodiments, the BChE is affinity purified after the step of eluting from the anion exchange material. In some embodiments, the affinity ligand is selected from the group consisting of a monoclonal antibody, a cocaine analog, and procainamide.

In some embodiments, the biological source is in liquid form and filtered before application to the anion exchange material. In some embodiments, the biological source material is subjected to solvent-detergent treatment. In some embodiments, the biological source is Cohn fraction IV, wherein the Cohn fraction IV is contacted with a fumed silica compound, adjusted to pH 4.0-4.5, and filtered through a filter media.

In some embodiments, the anion exchange group (i.e., the functional group) is attached to a membrane or a resin. In some embodiments, the anion exchange group is attached to a membrane. In some embodiments, the anion exchange group is a quaternary amine (Q) or diethylaminoethane (DEAE). In some embodiments, two or more anion exchange membranes are connected in series.

In some embodiments, the total protein applied to the anion exchange membrane is at least 1000 mg/ml of membrane volume. In some embodiments, the total protein applied to the membrane is at least 1500, 2000, 2500, 3000, 4000 or more mg/ml of membrane volume.

In some embodiments, the flow rate for the applying step is at least 1.5 times membrane volume, e.g., at least 2, 2.5, 3, 3.5, 4, 4.5, 5, 5.5, 6, or more, per minute. In some embodiments, the biological source material applied to the anion exchange material has a conductivity of 2.8 mS/cm or less. In some embodiments, the conductivity of the wash buffer is 3.8 mS/cm or less. In some embodiments, the conductivity of the elution buffer is 5.6 mS/cm or more.

DETAILED DESCRIPTION OF THE INVENTION

Figure 1:
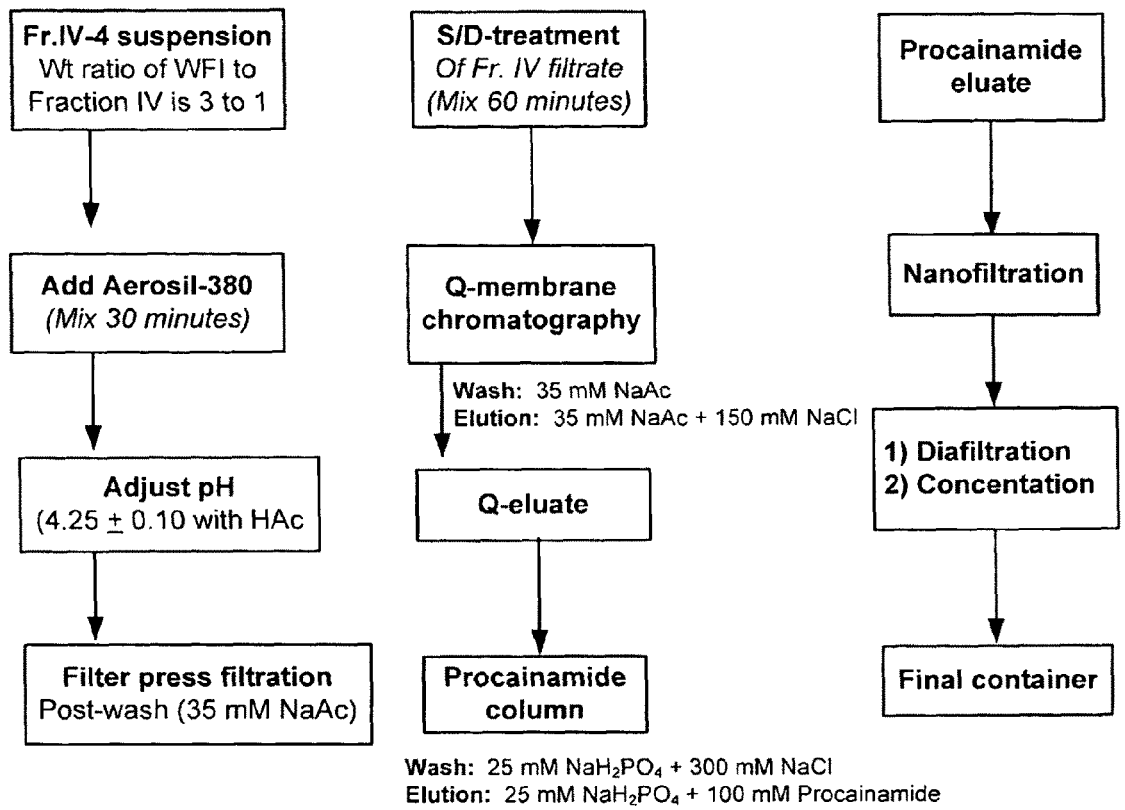
FIG. 1 is a flowchart of the purification scheme used in the Examples.

Cholinesterases are used as bioscavengers to counteract the toxic effects of cocaine and organophosphates such as sarin and other chemical warfare agents. The invention provides for efficient enrichment of butyrylcholinesterase (BChE) from biological sources.

A. DEFINITIONS

Butyrylcholinesterase (BuChE) is also referred to as non-specific cholinesterase, plasma cholinesterase, and pseudo-cholinesterase. The human enzyme (referred to as hBuChE or Hu BuChE) exists as a tetramer of 340 kD in plasma. Each monomer has 3 inter-chain disulphide bridges. Two monomers form a dimer via a disulphide linkage at cysteine 571, and two dimers, in turn, form a tetramer via hydrophobic interactions. As used herein, BuChE broadly refers to the tetrameric, dimeric, and monomeric forms, as well as polypeptides and multimers that are substantially identical to the Hu BuChE polypeptides described in Accession Nos. P06276.1 and Q96HL2.

As used herein, a "biological sample" or "biological source" includes organs and tissues, such as biopsy and autopsy samples, and frozen sections. Biological sources include blood (including blood fractions), sputum, tissue, cultured cells, e.g., primary cultures, explants, and transformed cells, urine, etc. Biological sources can be either prokaryotic (e.g., a recombinant bacterial cell) or eukaryotic, e.g., a recombinant cell, a mammal (such as a primate, chimpanzee, human, cow, dog, cat, a rodent, guinea pig, rat, mouse, rabbit), a bird, reptile, fish, or recombinant plant.

As used herein, "anion exchange" refers to methods of separating proteins based on charge-charge interactions. Generally, the functional anion exchange group is immobilized on a solid or semi-solid matrix, e.g., on a resin or membrane. For anion exchange, the immobilized functional group is positively charged and thus preferentially retains negatively charged proteins. Examples of anion exchange functional groups are quaternary amine (Q) and diethylaminoethane (DEAE).

Other suitable cationic functional groups (anion exchangers) include aminoethyl (AE-derivatized matrices); dimethylaminoethyl (DMAE-derivatized matrices); trimethylaminoethyl (TMAE-derivatized matrices); diethyl-(2-hydroxypropyl)aminoethyl (QAE-derivatized matrices) and similar groups. Commercially available cationic anion exchange matrices include: DEAE SEPHADEX (Pharmacia Biotech AB or "PB"), DEAE SEPHACEL (PB), DEAE SEPHAROSE FAST FLOW (PB), DEAE SEPHAROSE CL-6B (PB), DEAE SEPHACEL (PB), DEAE POROS (Perceptive BioSystems), QAE CELLEX (BioRad), QAE SEPHADEX (PB), Q SEPHAROSE FAST FLOW (PB), DEAE BIO-GEL A (BioRad), DEAE Cellulose (Whatman, Pierce), AG & Biorex Styrene/Divinyl Benzene Resins (BioRad), Anion exchange Macro-Prep Supports (BioRad), Fractogel® EMD DEAE, TMAC, or DEAE (E. Merck), TOYOPEARL DEAE (TosoHaas), TOYOPEARL-QAE (TosoHaas), Q HyperD® (BioSepra), DEAE TRIS ACRYL® (BioSepra), DEAE SPHEROSIL® (BioSepra).

As used herein, "affinity chromatography" refers to a separation method that is specific for a particular protein or site on a protein. The functional affinity ligand is immobilized on a solid or semi-solid matrix. Examples of affinity ligands include antibodies and antibody fragments, natural ligands or ligand analogs (e.g., for a particular receptor), and natural binding partners or analogues thereof (e.g., for a multisubunit complex). In the case of BChE, affinity ligands include cocaine analogues, procainamide, organophosphorous compounds, and BChE-specific antibodies. The affinity ligands may include ion exchange functionalities such as acidic functionalities for binding positively charged proteins, or basic functionalities for binding negatively charged proteins. Examples include, without limitation, amino (e.g., secondary, tertiary) and quaternary amino groups, carboxyl groups, sulfonic acid groups, etc. Affinity ligands such as aldehyde and epoxy functionalities are useful to bind target species containing hydroxyl, amino and thiol groups. Affinity ligands and methods of binding them to solid support materials are well known in the purification art. See, e.g., the reference texts Affinity Separations: A Practical Approach (Practical Approach Series), Paul Matejtschuk (Editor), Irl Pr: 1997; and Affinity Chromatography, Herbert Schott, Marcel Dekker, New York: 1997.

The term "wash buffer" refers to a buffer used to wash or re-equilibrate the ion exchange or affinity purification material, prior to eluting the polypeptide molecule of interest. The wash buffer and loading buffer can employ the same matrix, but this is not required.

The "elution buffer" is used to elute (remove) the polypeptide of interest from the ion exchange or affinity purification material. The conductivity and/or pH of the elution buffer is/are such that the polypeptide of interest is eluted from the material.

The term "conductivity" refers to the ability of an aqueous solution to conduct an electric current between two electrodes. In solution, the current flows by ion transport. Therefore, with an increasing amount of ions present in the aqueous solution, the solution will have a higher conductivity. The unit of measurement for conductivity is milliSiemens/cm (mS/cm), and can be measured using a commercially available conductivity meter. The conductivity of a solution may be altered by changing the concentration of ions therein. For example, the concentration of a buffering agent and/or concentration of a salt (e.g., NaCl or KCl) in the solution can be altered in order to achieve the desired conductivity, as shown in the Examples herein.

As used herein, the term "filter" includes device employed for liquid-solid separation by mechanical entrapment and electrokinetic absorption (for example membrane filtration, depth filtration dialysis, ultrafiltration, diafiltration, and nanofiltration). Filter materials include cellulose, silica compounds, cloth, paper, porous porcelain, charcoal, etc. through which liquid is passed to separate suspended impurities, or materials of different sizes and/or weights.

Specific examples include Zeta Plus depth filter media (Cuno Corp), and Seitz depth filter media (Pall Corp.)

The term "percent recovery," as used herein, refers to the amount of protein recovered from a particular separation or purification step, expressed as a percentage. For example, percent recovery can compare the total amount of protein applied to a separation step to the total amount of protein recovered, e.g., by elution, from the separation. Percent recovery can be measured for a particular protein by comparing the total amount of that protein applied to the separation step to the total amount recovered, e.g., by specific detection by size, immunoaffinity, or activity assay.

"Substantial identity" or "substantial homology" means that two peptide sequences, when optimally aligned, such as by the programs GAP or BESTFIT using default gap weights, share at least 65 percent sequence identity, e.g., at least 80, 85, 90, 92, 95, 96, 97, 98 or 99 percent sequence identity. Residue positions which are not identical generally differ by conservative amino acid substitutions.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases. In this manner, operable linkage of different sequences is achieved. It is understood that once a recombinant nucleic acid is made and reintroduced into a host cell or organism, it will replicate non-recombinantly, i.e., using the in vivo cellular machinery of the host cell rather than in vitro manipulations. Similarly, a "recombinant protein" is a protein made using recombinant techniques, i.e., through the expression of a recombinant nucleic acid as depicted above.

The term "transgenic" is used to describe a cell or organism generated using recombinant methods. Generally, a transgenic cell or organism will carry a "transgene," or non-endongenous nucleic acid.

The phrase "specifically (or selectively) binds" to an antibody or other compound, refers to a binding reaction that is determinative of the presence of the protein, often in a heterogeneous population of proteins and other biologics. Thus, under designated assay conditions, the specified compound or antibody binds to the protein at least two times the background and more typically more than 10 to 100 times background. Specific binding to an antibody under such conditions requires an antibody that is selected for its specificity for a particular protein. For example, polyclonal antibodies raised to BChE monomer or complex polypeptide, polymorphic variants, alleles, orthologs, and conservatively modified variants, or splice variants, or portions thereof, can be selected to obtain only those polyclonal antibodies that are specifically immunoreactive with BChE, and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

B. BUTYRYLCHOLINESTERASE

Butyrylcholinesterase (BChE) exists as a tetramer of 340 kD in blood plasma. BChE metabolizes cocaine, heroin, and toxic organophosphantes, and is useful for preventing and reducing intoxication and toxicity (see, e.g., Raveh et al. (1993) *Biochem. Pharmacol.* 45:2465-74; Mattes et al. (1996) *Pharmacol. Lett.* 58:257-61). BChE has also been shown to bind beta-amyloid fibrils (Podoly et al. (2008) *Neurodeger. Dis.* 5:232-36).

In some embodiments, BChE is modified to improve its retention time in circulation. This is particularly useful for prophylactic uses, where the timing and duration of toxin exposure is uncertain. Attachment of a pharmaceutically acceptable, water soluble polymer, such as polyethylene glycol (PEG) improves the enzyme's retention time in vivo. Exemplary polymers include pharmaceutically acceptable PEG mixtures, mono-activated alkoxy-terminated polyalkylene oxides, dextran, polyvinyl pyrrolidones, polyacrylamides, polyvinyl alcohols, and carbohydrate-based polymers. Methods of attachment are described, e.g., in WO02/087624. For example, the primary amines in BChE can be targeted with activated methoxy-PEG in molar excess. In some cases, mean retention time of the enzyme can be increased 5-, 10-, and even 50-fold, as compared to unmodified BChE.

BChE can be either naturally-occurring, i.e., isolated from endogenous sources, or produced recombinantly. Endogenous sources include human, rabbit, rat, bovine, horse, sheep, etc. Generally, BChE is isolated from blood or blood fractions, but BChE can be isolated from tissue or organ extracts as well (e.g., liver, spleen, lung, bone marrow, kidney, placenta, etc.).

Blood preparations with significant levels of BChE include serum and plasma fractions. BChE can be isolated from subfractions of these elements as well. One well-known blood separation technique is Cohn fractionation, as described in Harris, *Blood Separation and Plasma Fractionation* Wiley-Liss (1991). According to Cohn's method (and recent variations thereof), blood proteins are separated into five fractions based on varying ethanol concentration, pH, and temperature. BChE is concentrated in Fraction IV, and in certain subfractions of Fraction IV (e.g., IV-4, IV-6). Cohn fractions can be stored frozen, as pastes, and can be resuspended for use in the methods of the invention.

Recombinant techniques can be advantageous for producing BChE on a large scale. Such techniques are well known in the art, and are generally described, e.g., in Ausubel et al., *Current Protocols in Molecular Biology* (1995 supplement); and Sambrook et al. MOLECULAR CLONING: A LABORATORY MANUAL, 2nd Ed., (1989). Briefly, an expression cassette comprising a polynucleotide sequence encoding BChE, operably linked to promoter, is introduced into a cell under conditions that are favorable for BChE expression.

*E. coli* is a useful prokaryotic host cell for recombinant expression techniques. Other microbial hosts suitable for use include bacilli, such as *Bacillus subtilis*, and other enterobacteriaceae, such as *Salmonella, Serratia*, and various *Pseudomonas* species. A recombinant expression vector is introduced into the prokaryotic hosts, generally containing expression control sequences compatible with the host cell (e.g., an origin of replication). In addition, any number of a variety of well-known promoters can be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation.

Other microbes, such as yeast (e.g., *Saccharomyces*), can also be used for expression. Yeast have a host of suitable vectors with expression control sequences, such as promoters, including 3-phosphoglycerate kinase or other glycolytic enzymes, and an origin of replication, termination sequences and the like as desired.

Plants and plant cell cultures can also be used for recombinant expression of BChE (Larrick and Fry, *Hum. Antibodies Hybridomas* 2:172-189 (1991); Benvenuto et al., *Plant Mol. Biol.* 17:865-874 (1991); During et al., *Plant Mol. Biol.* 15:281-293 (1990); Hiatt et al., *Nature* 342:76-78 (1989)). Plant hosts include, for example: *Arabidopsis, Nicotiana tabacum, Nicotiana* rustica, and *Solanum tuberosum*. An exemplary expression cassette is the plasmid pMOG18, e.g., according to the method of Sijmons et al., *Bio/Technology* 8:217-221 (1990). *Agrobacterium tumifaciens* T-DNA-based vectors can also be used for expressing BChE-encoding sequences; preferably such vectors include a marker gene encoding spectinomycin-resistance or another selectable marker.

Insect cell culture can also be used to express BChE, typically using a baculovirus-based expression system, e.g., according to the methods of Putlitz et al., *Bio/Technology* 8:651-654 (1990).

In addition to microorganisms and plants, mammalian cell culture can also be used to express and produce the polypeptides of the present invention (see Winnacker, "From Genes to Clones", VCH Publishers, New York (1987)). Mammalian cells include HEK-293 cells the CHO cell lines, various COS cell lines, HeLa cells, myeloma cell lines, etc. (see, e.g., Lynch et al. (1997) *Toxicol. Appl. Pharmacol.* 145:363-71 for expression of BChE in HEK cells). Expression vectors for these cells can include expression control sequences, such as an origin of replication, a promoter, an enhancer (Queen et al., *Immunol. Rev.* 89:49-68 (1986)), and necessary processing information sites, such as ribosome binding sites, RNA splice sites, polyadenylation sites, and transcriptional terminator sequences. Expression control sequences include promoters derived from SV40, adenovirus, bovine papilloma virus, cytomegalovirus and the like. A selectable marker, such as a neo expression cassette, can also be included in the expression vector.

BChE can also be expressed and purified from the milk of a transgenic mammal. Such techniques are described, e.g., in U.S. Pat. No. 7,045,676. General strategies and exemplary transgenes employing aS1-casein regulatory sequences for targeting the expression of a recombinant protein to the mammary gland are described in more detail in WO 91/08216 and WO 93/25567. Additional examples of transgenes employing mammary gland specific regulatory sequences include Simon et al., *Bio/Technology* 6:179-183 (1988) and WO88/00239 (1988); EP 279,582 and Lee et al., *Nucleic Acids Res.* 16:1027-1041 (1988).

C. PROTEIN PURIFICATION TECHNIQUES

Protein purification techniques include, for example, methods utilizing solubility (such as salt precipitation and solvent precipitation), methods utilizing the difference in molecular weight (such as dialysis, ultra-filtration, gel-filtration, and SDS-polyacrylamide gel electrophoresis), methods utilizing a difference in electric charge (such as ion-exchange column chromatography), methods utilizing specific interaction (such as affinity chromatography), methods utilizing a difference in hydrophobicity (such as reversed-phase high performance liquid chromatography) and methods utilizing a difference in isoelectric point (such as isoelectric focusing electrophoresis). Reference resources include: Scopes, *Protein Purification Principles and Practice*, Springer Press, 3d edition (1994) and Abelson et al., *Methods in Enzymology, Volume* 182*: Guide to Protein Purification*, Academic Press (1990).

Proteins expressed in bacteria may form insoluble aggregates ("inclusion bodies"). Several protocols are suitable for purification of BChE inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., *Molecular Cloning, A Laboratory Manual* (2nd ed. 1989); Ausubel et al. *Current Protocols in Molecular Biology* (1995 supplement)).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. BChE polypeptides are separated from other bacterial proteins by standard separation techniques, e.g., with Ni-NTA agarose resin.

Alternatively, it is possible to purify BChE polypeptides from bacteria periplasm. After lysis of the bacteria, when BChE is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Often as an initial step, particularly if the protein mixture is complex, an initial salt fractionation can separate many of the unwanted host cell proteins (or proteins derived from the cell culture media) from the recombinant protein of interest. Ammonium sulfate is commonly used, as it precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of BChE or BChE complex polypeptides can be used to isolate them from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retained portion of the ultrafiltration is then ultrafiltered against a membrane with a molecular cut off greater than the molecular weight of the protein of interest. The recombinant protein will pass through the membrane into the filtrate. The filtrate can then be subjected to further separation and purification techniques.

BChE polypeptides can be separated from other proteins on the basis of its size, net surface charge, hydrophobicity, and affinity for substrate and ligands. In addition, antibodies raised against BChE proteins can be conjugated to column matrices and the proteins immunopurified. Chromatography methods that can be used for these techniques (such as FPLC and HPLC) are known in the art. It will be apparent to one of skill that chromatography can be performed at any scale and using equipment from many different manufacturers (e.g., Pharmacia Biotech).

Ion exchange can be used to separate proteins based on net charge. BChE is negatively charged at standard pHs, and is advantageously subjected to anion exchange chromatography. In one embodiment the pH is adjusted to 4.0-4.5 for binding. In another embodiment the pH is adjusted to 4.15-4.35. Examples of functional anion exchange groups are DEAE and mono Q. MonoQ provides a true ionic interaction without interference of hydrogen binding or electrostatic interactions with the protein. Conjugated forms of these materials are commercially available, e.g., from Pall, Sartobind, Pharmacia Biotech, and Sigma-Aldrich.

Ion exchange is highly sensitive to pH, and, ideally, the pH is at least one unit higher than the isoelectric point of the protein of interest. A titration curve using the protein of interest is generally run to determine the best pH for optimal binding between the functional group and the protein. Exemplary buffers commonly used in the ion exchange of proteins are Acetic, Citric, Mes, Phosphate, Hepes, L-histidine, Imidazole, Tris, Diethanolamine. Suitable counterions include sodium, potassium, chloride, bromine, hydrogen, acetate, and maleate. Varying amounts of salt, e.g., sodium chloride, can be added to the buffer as described below. The buffering pH range of the above mentioned buffers is from 4.0 to 8.8. In one embodiment, acetate is used as the wash buffer with one or more washed including sodium chloride. In one embodiment, 35 mM sodium acetate is used with 20 mM sodium chloride and 150 mM sodium chloride, respectively. In another embodiment, a single wash of 35 mM sodium acetate with 150 mM sodium chloride is used.

The conductivity of the solution applied to the anion exchange media is also important for optimal binding, and can be varied by changing the salt concentration of the solution. Conductivity of the wash buffer is also generally optimized for optimal washing of the impurities and unwanted proteins, while retaining binding of the protein of interest. Elution buffers for anion exchange generally have higher conductivity in order to disrupt the ionic interaction between the protein and the functional group. These principles are illustrated in more detail in the examples below.

BChE polypeptides can also be separated from other materials based on their affinity for substrate, ligands, specific antibodies, or specific antibody fragments.

BChE can be purified using procainamide conjugated, e.g., to a resin, membrane, or other immobile media. Methods of generating procainamide-sepharose resin and separation of BChE are described, e.g., in Grunwald et al. (1997) *J Biochem Biophys Methods* 34:123-35 and Lockridge & La Du (1978) *J. Biol. Chem.* 253:361-66. Elution of BChE can be accomplished by addition of free procainamide, which is separated later.

A number of antibodies specific for BChE are known in the art and commercially available. These include 002-01, 6F41, 3E8, C-15, C-18, N-13, and HPA001560, available from Santa Cruz Biotechnology and Sigma-Aldrich. Any of these antibodies or specific BChE-binding fragments thereof can be bound to an immobilized substrate for use in purification as is known in the art.

D. METHODS OF STORAGE

Proteolysis of BChE can transform the tetramer into dimers and monomers with free SH groups, which will accelerate the clearance of BChE from blood. Thus, it is important to store purified BChE in controlled conditions, in a suitable buffering solution. For example, BChE can be stored for a number of months at 4 C in Tris buffer, pH 7.4-8.0, or phosphate buffer, pH 7.4-8.0, with 1 mM EDTA (see e.g., Grunwald et al. (1997) *J Biochem Biophys Methods* 34:123-35). BChE can also be lyophilized or freeze-dried and stored for several months without significant loss of activity. Methods of storing proteins, and appropriate buffering systems are known in the art.

E. METHODS OF DETERMINING PROTEIN QUANTITY AND PURITY

Protein concentration can be determined using standard methods, such as the Lowry method using a BSA or other standard calibration (see, e.g., Scopes, supra; Grunwald, supra). Concentration and content of a protein solution can also determined by gel or capillary electrophoresis.

F. METHODS OF DETERMINING CHOLINESTERASE ACTIVITY

Cholinesterases can bind to nerve gases (e.g., soman, sarin, tabun, VX), pesticides, cocaine, and heroin, and catabolize the compounds. Substrate binding and binding kinetics can be measured by any technique known in the art, e.g., using a detectably-labeled analogue of a targeted compound (see, e.g., Lockridge & Du Lu (1978) *J. Biol. Chem.* 253:361-66). Hydrolytic activity of BChE is generally measured using the technique of Ellman et al. (1961) *Biochem Pharmacol* 7:88-95. Briefly, BChE is added to BTC in phosphate buffer at pH 8.0 at room temperature. One unit activity is generally expressed as the amount of enzyme required to hydrolyze 1 μmol/min. BChE activity can also be tested using different substrates, e.g., cocaine or benzoylcholine (see Mattes et al. (1996) *Pharmacol. Lett.* 58:257-61; Lockridge & Du Lu, supra). Activity can be titrated, e.g., by titrating a solution with unknown BChE concentration.

G. EXAMPLES

1. Materials and Methods

The following studies represent scaled down evaluations of replacement of Q Hyper D anion exchange resin with a Q membrane for purification of BChE. Pall Mustang and Sartorius MA membranes were tested during the anion exchange purification step. The membrane parameters are described in Table 1.

TABLE 1

| | | Units | Pall Mustang Q XT5 | Sartorius Sartobind MA 100 | Sartorius Sartobind MA 15 |
|---|---|---|---|---|---|
| Membrane material | | | Modified hydrophilic polyethersulfone | Reinforced stabilized cellulose | |
| Technical parameters | Effective absorption area | cm² | N/A | 100 | 15 |
| | Bed height | mm | 2.2 | 1.40 | 0.80 |
| | Bed volume | mL | 5 | 2.75 | 0.41 |
| | Layers | | N/A | 5 | 3 |
| | Pore size | um | N/A | >3 | >3 |
| Operational conditions | Flow rate | mL/min | 50 | >75 | >50 |
| | Maximum operating pressure | psi | 75 | 87 | |
| | Pre-conditioning | | 2M NaCl; 0.5M HAc, 0.5N NaOH | | |
| | Usage | | Reusable | Reusable | Reusable |
| Storage conditions | | | 0.1 M NaOH + 1M NaCl | 20% Ethanol + 0.9% NaCl | |

The present feasibility study was conducted in order to get a deeper understanding of a Q-membrane chromatography step in place of the anion exchange chromatography for purification of BuChE. We found that membrane chromatography enhances recovery and minimizes loss of product with respect to the following critical process parameters: flow rate, membrane volume, and total protein (TP) load.

Each scale-down run consisted of the following steps, as outlined in FIG. 1:
(1) One part Cohn Fraction IV-4 precipitate is suspended in three parts (or more) water for injection (WFI) and mixed;
(2) Fumed silica (Aerosil) is added to the suspension and the pH is adjusted to 4.15 to 4.35 with 5N acetic acid;
(3) The suspension is then filtered via Cuno filter pads in a filter press using 35 mM Sodium Acetate, pH 4.15 to 4.35 as the postwash buffer;
(4) Solvent/Detergent (SD) mixture is added to the filtrate; and
(5) Q membrane chromatography is performed using membranes with bed volumes of 5 mL, 2.75 mL, and 0.41 mL for each successive set of runs.

These basic process parameters were adjusted for each membrane experiment as follows:

Run #1

Runs #1-9 were run separately from Runs #10-11. Run 1 was a repeat of Run #11 (below) using a new preparation of Cohn fraction IV (Fr. IV-4) filtrate and a new Pall Q Mustang membrane. Both the buffer and the load material were diluted with WFI to a conductivity of 1.7 mS/cm. Total protein load was 1635 mg per mL of membrane volume (MV). Flow rate was 3.2 MV/min (15.9 mL/min). Protein was eluted with 35 mM sodium acetate buffer with two concentrations of NaCl: 20 mM followed by 150 mM Run #2

The Pall Q Mustang 5 mL membrane from the previous experiment (Run #1) was reused. No dilutions were performed on either the buffer or the load material (conductivity of buffer was 3.1 mS/cm and load material was 2.8 mS/cm). Total protein load was 1080 mg per mL of membrane volume (MV). Flow rate was 3.2 MV/min (15.9 mL/min). Protein was eluted with 35 mM sodium acetate buffer and 150 mM NaCl.

Run #3

A new Sartorius X100 2.75 mL membrane was used. The buffer and the load material were undiluted (conductivity of buffer was 3.7 mS/cm and load material was 2.6 mS/cm). Total protein load was 2335 mg per mL of membrane volume. Flow rate was 5.8 MV/min (15.9 mL/min). Protein was eluted with 35 mM sodium acetate buffer and 150 mM NaCl.

Run #4

The Sartorius X100 2.75 mL membrane from the previous experiment (Run #3) was reused. Both the buffer and load material were diluted with WFI to a conductivity of 1.7 mS/cm. Total protein load was 1301 mg per mL of membrane volume. Flow rate was 1.5 MV/min (4.0 mL/min). Protein was eluted with 35 mM sodium acetate buffer and 150 mM NaCl.

Run #5

A new Sartorius X100 2.75 mL membrane was used. No dilutions were performed on either the buffer or the load material (conductivity of buffer was 3.8 mS/cm and load material was 2.7 mS/cm). Total protein load was 2246 mg per mL of membrane volume. Flow rate was 2 to 4.4 MV/min (5.5 to 12.0 mL/min). Protein was eluted with 35 mM sodium acetate buffer and 150 mM NaCl.

Run #6

A new Sartorius X15 0.41 mL membrane was used. The buffer and the load material were undiluted (conductivity of buffer was 3.8 mS/cm and load material was 2.7 mS/cm). Total protein load was 2098 mg per mL of membrane volume. Flow rate was 4.1 MV/min (1.7 mL/min). Protein was eluted with 35 mM sodium acetate buffer and 150 mM NaCl.

Run #7

This was a repeat of the previous experiment (Run #6) using the same Sartorius X15 0.41 mL membrane. Total protein load was 2167 mg per mL of membrane volume.

Run #8

This was a repeat of the previous experiments (Runs #6 and #7) using the same Sartorius X15 0.41 mL membrane. Total protein load was 2169 mg per mL of membrane volume.

Run #9

This was a repeat of the previous experiments (Runs #6 to #8) using the same Sartorius X15 0.41 mL membrane. Total protein load was 2295 mg per mL of membrane volume.

Run #10

Run #10 was run alongside a similar isolation scheme using Q anion exchange column chromatography, described below. In Run #10, a new Pall Q Mustang 5 mL membrane was used. The 35 mM Sodium Acetate, pH 4.2 buffer was diluted with WFI to a conductivity of 1.9 mS/cm and used for equilibration and wash. The load material (SD treated IV-4 filtrate) was diluted with WFI to a conductivity of 1.8 mS/cm prior to loading. Total protein load was 4844 mg per mL of membrane volume. Flow rate was 3.2 MV/min (15.9 mL/min). Protein was eluted with 35 mM sodium acetate buffer with two concentrations of NaCl: 20 mM followed by 150 mM.

Run #11

The Pall Q Mustang 5 mL membrane from the previous experiment (Run #10) was reused. Both the buffer and the load material were diluted with WFI to a conductivity of 1.7 mS/cm. Total protein load was 1273 mg per mL of membrane volume. Flow rate was 3.2 MV/min (15.9 mL/min). Protein was eluted with 35 mM sodium acetate buffer with two concentrations of NaCl: 20 mM followed by 150 mM.

Results of the above isolation scheme were compared to those using anion exchange column chromatography. The column chromatography was carried out on Q Hyper D anion exchange resin alongside membrane Run #10, described above. Similar to the membrane isolation, the column isolation scheme started with solvent-detergent treatment of Aerosil filtrate. The Q-media column was flushed with 2M NaCl, 0.5M acetic acid, and 0.5N NaOH prior to equilibration with 35 mM Sodium Acetate, pH 4.25. After that, the solvent-detergent treated filtrate was loaded onto the column. The column was then washed with 35 mM Sodium Acetate, pH 4.25, then the sodium acetate buffer with 20 mM NaCl to wash out impurities. Elution was performed with sodium acetate buffer with 150 mM NaCl. Once the protein has eluted, the column can be regenerated with 2 M NaCl, 0.5 M acetic acid, and 0.5N NaOH and stored in 20% EtOH with 1M NaCl.

2. Results

Table 2 provides a summary of the results described below. The following abbreviations are used: MV=membrane volume (also column volume); Cond=conductivity; TP=total protein; Spec. activity=specific BChE activity; LFT=load flow through; and WFT=wash flow through, Total balance=BChE activity in LFT+WFT+Eluate as % of loaded activity.

TABLE 2

| | | Loading conditions | | | | | | | BChE activity | | | | |
|---|---|---|---|---|---|---|---|---|---|---|---|---|---|
| | | | Flow rate | | TP, | TP loaded | | Wash | Elution | | | Loss in | Total | Spec. |
| Run | Media | MV (ml) | MV/ min | ml/ min | conc mg/ml | mg/ml of MV | Cond mS/cm | Cond mS/cm | Cond mS/cm | Input U/ml | Recovery % | LFT + WFT % | balance % | activity U/mg |
| | Q Hyper D Gel | 64/82 | 0.1-0.25 | | 7.8-13.7 | 360-600 | 1.4-3.0 | | | 4.2-7.2 | 38-57 | 20-42 | 66 to 80 | 52-170 |
| 10 | Pall | 5 | 3.2 | 15.9 | 12.1 | 4844 | 1.8 | 1.9 | 5.6-18 | 7.0 | 42.8 | 49.8 | 96 | 84 |
| 11 | | | | | 12.6 | 1273 | 1.7 | 1.7 | 5.6-18 | 7.2 | 64.4 | 17.3 | 89 | 56 |
| 1 | | | | | 5.2 | 1635 | 1.7 | 1.7 | 7.5-22.7 | 2.1 | 64.3 | 27.5 | 92 | 27 |
| 2 | | | | | 9.0 | 1080 | 2.8 | 3.1 | 22.7 | 4.0 | 51.1 | 36.1 | 87 | 59 |
| | Range for Pall | | | | 5.2-12.6 | 1080-4844 | 1.7-2.8 | 1.7-3.1 | 5.6-22.7 | 2.1-7.2 | 42.8-64.4 | 17.3-49.8 | 87-96 | 27-84 |
| | Average for Pall | | | | | | | | | | 55.7 | 32.7 | 91 | 56 |
| 3 | Sartor. | 2.75 | 5.8 | 15.9 | 10.7 | 2335 | 2.6 | 3.7 | 23 | 4.2 | 71.4 | 32.2 | 104 | 70 |
| 4 | | | 1.5 | 4.0 | 4.9 | 1301 | 1.7 | 1.7 | 23 | 2.2 | 43.2 | 31.4 | 75 | 53 |
| 5 | | | 2-4.4 | 5.5-12 | 10.3 | 2246 | 2.7 | 3.8 | 23 | 4.1 | 43.6 | 36.4 | 80 | 87 |
| | Range for Sartorius 2.75 ml | | | | 4.9-10.7 | 1301-2335 | 1.7-2.6 | 1.7-3.8 | 23 | 2.2-4.2 | 43.2-71.4 | 31.4-36.4 | 75-104 | 53-87 |
| | Average for Sartorius 2.75 ml | | | | | | | | | | 52.7 | 33.3 | 86 | 70 |
| 6 | Sartor. | 0.41 | 4.1 | 1.7 | 10.0 | 2098 | 2.7 | 3.8 | N/R | 3.6 | 46.9 | 44.1 | 91 | 59 |
| 7 | | | 3.7 | 1.5 | 10.3 | 2167 | | | | no data | no data | no data | no data | no data |
| 8 | | | 3.4 | 1.4 | 10.3 | 2169 | | | | 3.8 | 35.8 | 36.8 | 73 | 44 |
| 9 | | | 3.4 | 1.4 | 10.9 | 2295 | | | | 3.6 | 46.1 | 42.7 | 89 | 59 |
| | Range for Sartorius 0.41 ml | | | | 10.0-10.9 | 2098-2295 | | | | 3.6-3.8 | 35.8-46.9 | 36.8-44.1 | 73-91 | 44-59 |
| | Average for Sartorius 0.41 ml | | | | | | | | | | 42.9 | 41.2 | 84 | 54 |

Figure 2:
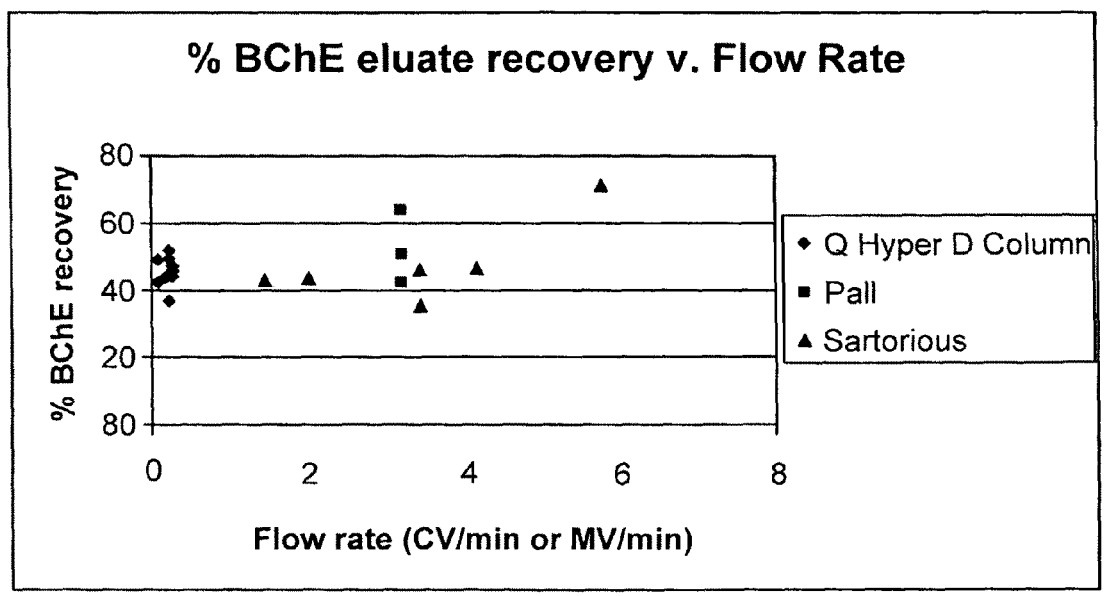
FIG. 2 is a graph comparing the Q Hyper D Column to the Pall and Sartorius Q-membranes for recovery of BChE vs. flow rate. Flow rate is expressed as either Column Volume per minute (CV/min) or Membrane Volume per minute (MV/min).

We compared BChE recoveries between the column and various Q-membranes based on flow rate through the media. As seen in FIG. 2, significantly higher flow rates were observed in membranes as compared to column without negative impact on BChE recovery. It was deduced that flow rates for membranes could be more than 10 times higher than those for columns. The advantage of using membranes lies in the reduced time needed to carry out our runs, especially given the larger amount of protein loaded onto the membranes (see Table 2). Hence, recovery is not compromised on either.

Figure 3:
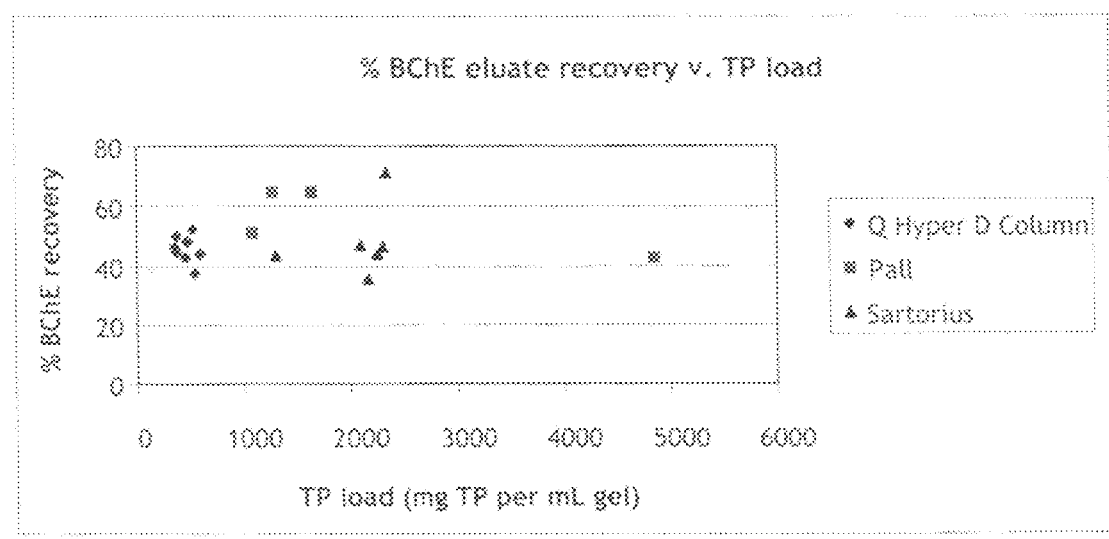
FIG. 3 illustrates a comparison of the three anion exchange media for recovery of BChE vs. total protein (TP) load. TP is expressed as mg protein loaded per mL column or membrane volume.

We next compared the Q-column to the Pall and Sartorius membranes for the amount of BChE recovered versus the total protein (TP) loaded. See FIG. 3. The columns are limited as to the amount of protein that can be loaded without compromising retention of the total amount protein loaded on the gel. Loss of retention would result in BChE losses in LFT and low BChE % recovery. The membranes, however, can accommodate much larger amounts of protein without loss of recovery, as shown in FIG. 3. Table 2 provides a side-by-side comparison of TP loads, and shows that up to 10 times as much protein could be loaded onto the membranes. Hence, retention of TP load is more efficient in the membranes than the column.

Figure 4:
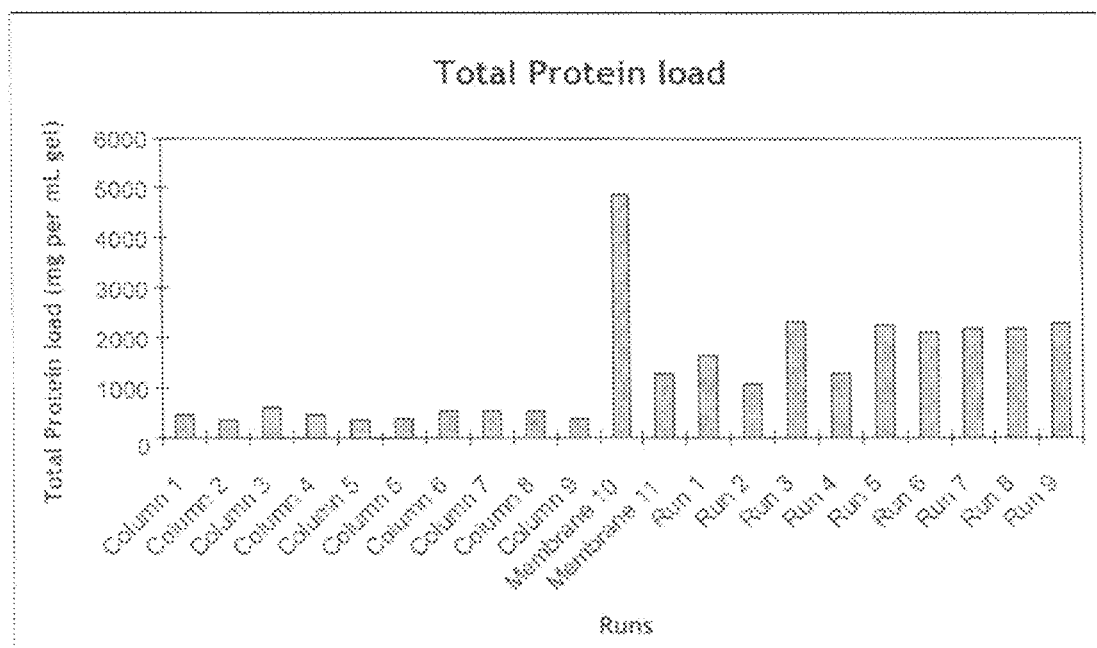
FIG. 4 compares the total protein load for the columns and membrane runs described in the Examples. The figure illustrates one of the advantages of the present method, namely that the membranes can support loading much larger amounts of protein than columns per ml of bed volume.

FIG. 4 provides further support for this advantage of membrane purification. FIG. 4 shows the amount of TP loaded for all of the runs (Q-column runs, Pall runs, and Sartorius runs). As shown in for "Membrane 10" (corresponding to Run #10 above), more than 5 times as much protein could be loaded on the membrane.

Figure 5:
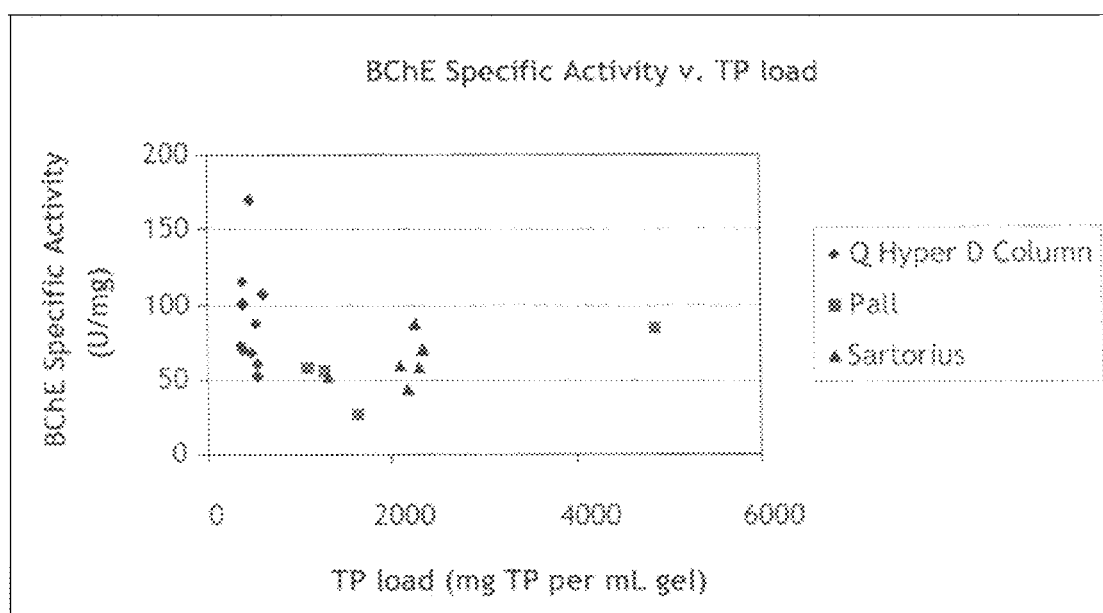
FIG. 5 compares the BChE specific activity vs. TP load for each purification. Specific activity is described as units BChE/mg protein.

FIG. 5 compares the BChE specific activity recovered from each of the runs. We found that significantly higher protein load achieved for the membranes does not have a detrimental effect on the BChE specific activity.

Figure 6:
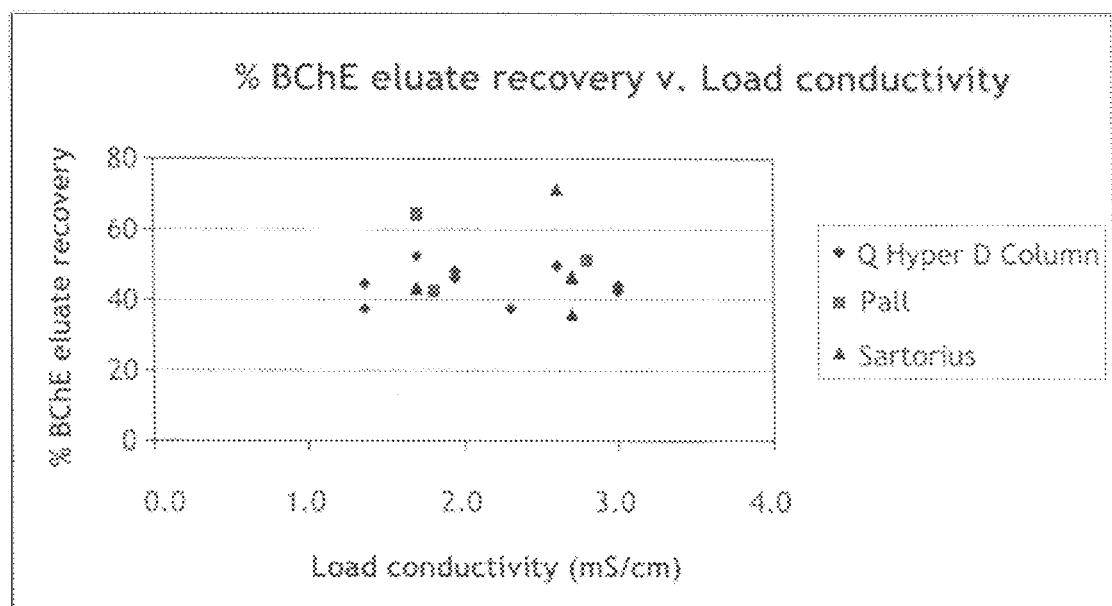
FIG. 6 illustrates the effect of conductivity of the protein loaded onto the membrane or column (load conductivity) on BChE recovery in eluate. Conductivity is expressed as mS/cm.

We next observed the effect of conductivity of the loaded protein solution on BChE recovery. As shown in FIG. 6, the conductivity of the initial protein solution was not correlated with recovery.

Figure 7:
FIG. 7 shows the percent BChE activity balance (BChE activity in LFT+WFT+Eluate as % of loaded activity) of the columns and membrane runs. The figure illustrates that significantly more BChE activity was accounted for in the membranes than in the columns.

FIG. 7 demonstrates another advantage of membranes over the columns for the anion exchange step. Significantly higher BChE activity balance (total BChE activity in LFT+WFT+Eluate as % of loaded activity) was observed in the membranes, indicating that more of the loaded BChE could be accounted for in the end. This observation leads to the possibility of significantly improving the BChE recovery, by connecting two or more Q membranes in series.

3. Conclusions

The above results indicated the following:

Membranes operated at significantly higher flow rates (0.1-0.25 CV/min in columns vs. 1.5-5.8 MV/min in membranes);

Membranes can withstand up to 10 times as much loaded protein;

Total BChE activity balance is more pronounced in membranes (91% for Pall membrane, 85% for Sartorius, and 73% for the columns); and Membranes did not require preparation of large quantities of buffers.

What is claimed is:

1. A method for making an enriched butyrylcholinesterase composition from a biological fluid having butyrylcholinesterase, the method comprising the steps of:

(A) contacting a biological fluid having butyrylcholinesterase with a fumed silica compound;

(B) adjusting the pH of the biological fluid contacted with the fumed silica compound in step (A) to a pH of from 4.15 to 4.35;

(C) filtering the pH adjusted biological fluid from step (B) to remove the fumed silica compound;

(D) applying the filtered biological fluid having butyrylcholinesterase from step (C) to a quaternary amine anion exchange material attached to a membrane equilibrated in with a buffer comprising acetate at a pH of from 4.15 to 4.35;

(E) washing the anion exchange material with a wash buffer comprising acetate;

(F) eluting butyrylcholinesterase from the anion exchange material by step elution with an elution buffer comprising acetate, thereby forming an enriched butyrylcholinesterase composition, wherein the butyrylcholinesterase content of the enriched butyrylcholinesterase composition is enriched at least 10 fold as compared to the starting biological fluid, as measured by butyrylcholinesterase activity per total protein; and (G) enriching butyrylcholinesterase eluted from the anion exchange material in step (F) using a procainamide affinity purification material, wherein the biological fluid in step (A) is a suspended Cohn Fraction IV.

2. The method of claim 1, further comprising solvent-detergent treatment of the filtered biological fluid having butyrylcholinesterase from step (C), prior to step (D).

3. The method of claim 1, wherein the total protein applied to the anion exchange membrane is at least 1000 mg per mL membrane volume.

4. The method of claim 1, wherein the total protein applied to the anion exchange membrane is at least 2000 mg per mL membrane volume.

5. The method of claim 1, wherein the butyrylcholinesterase content of the enriched butyrylcholinesterase composition is enriched at least 20 fold as compared to the starting biological fluid, as measured by butyrylcholinesterase activity per total protein.

6. The method of claim 1, wherein the butyrylcholinesterase content of the enriched butyrylcholinesterase composition is enriched at least 40 fold as compared to the starting biological fluid, as measured by butyrylcholinesterase activity per total protein.

7. The method of claim 1, wherein the butyrylcholinesterase content of the enriched butyrylcholinesterase composition is enriched at least 60 fold as compared to the starting biological fluid, as measured by butyrylcholinesterase activity per total protein.

8. The method of claim 1, butyrylcholinesterase is applied to the anion exchange material attached to a membrane at a flow rate of at least 1.5 times membrane volume per minute.

9. The method of claim 1, wherein the conductivity of the biological fluid applied to the anion exchange material attached to a membrane is 2.8 mS/cm or less.

10. The method of claim 1, wherein the anion exchange material attached to a membrane is a Q membrane, and at least two Q membranes are connected in series.

11. The method of claim 1, wherein the conductivity of the wash buffer in the washing step is 3.8 mS/cm or less.

12. The method of claim 1, wherein the conductivity of the elution buffer in the eluting step is at least 5.6 mS/cm.

13. The method of claim 1, wherein the membrane is in a series of two or more membranes.

* * * * *